United States Patent [19]
Holland

[11] Patent Number: 5,427,742
[45] Date of Patent: Jun. 27, 1995

[54] TISSUE PROCESSING CASSETTE

[76] Inventor: Wayne Holland, 2614 C St., Liberty Borough, Pa. 15133

[21] Appl. No.: 233,318

[22] Filed: Apr. 26, 1994

[51] Int. Cl.⁶ .............................................. C12M 3/00
[52] U.S. Cl. .................................. 422/102; 422/104; 422/99; 435/284; 435/297; 435/299
[58] Field of Search ........................ 422/102, 104, 99; 425/117; 435/284, 298, 297, 299; 211/126, 128, 187, 208; 249/83, 196

[56] References Cited

U.S. PATENT DOCUMENTS

| | | | |
|---|---|---|---|
| Re. 28,165 | 9/1974 | McCormick | 425/117 |
| 1,065,040 | 6/1913 | Garner | 18/26 |
| 2,996,762 | 8/1961 | McCormick | 18/26 |
| 3,319,289 | 5/1967 | McCormick | 18/5 |
| 3,411,185 | 11/1968 | Pickett | 18/34 |
| 3,456,300 | 7/1969 | Pickett | 18/5 |
| 3,674,396 | 7/1972 | McCormick | 425/117 |
| 3,940,219 | 2/1976 | Pickett et al. | 425/117 |
| 3,982,862 | 9/1976 | Pickett et al. | 425/117 |
| 4,557,903 | 12/1985 | McCormick | 422/101 |
| 4,569,647 | 2/1986 | McCormick | 425/117 |
| 4,801,553 | 1/1989 | Owen et al. | 436/174 |
| 4,975,377 | 12/1990 | Key | 435/284 |
| 5,061,452 | 10/1991 | Yamomoto et al. | 422/101 |
| 5,068,091 | 11/1991 | Toya | 422/99 |
| 5,080,869 | 1/1992 | McCormick | 422/102 |
| 5,139,951 | 8/1992 | Butz et al. | 435/284 |
| 5,269,671 | 12/1993 | McCormick | 425/117 |

Primary Examiner—Robert J. Warden
Assistant Examiner—N. Bhat
Attorney, Agent, or Firm—R. V. Westerhoff; Jonathan J. Wainer

[57] ABSTRACT

A tissue processing cassette adapted for processing small tissue specimens includes a base frame and a lid frame, each including a central opening and a face adapted to abut the face of the other in registered relationship in a closed position. A porous screen spans the central opening of each of the base frame and the lid frame, the screens being spaced apart when the cassette is closed, whereby the base frame, the lid frame and the screens define an enclosed area for holding a tissue specimen during preparation for histological examination. The porous screen permits processing fluids to flow through the enclosure, but resists entry of particulate contaminants into the enclosure, and also resists outflow of small tissue specimens from the enclosure during processing. The enclosure has an interior perimeter surface that includes no sharp corners that can trap a small specimen. An outer base frame, preferably about rectangular in shape to fit standard tissue specimen molds and microtomes, and having a substantially larger area than the central opening, includes a web, preferably rigid and porous, for supporting the base frame. In a second embodiment, the lid frame can also be supported by a web extending inwardly from a larger, preferably rectangular-shaped outer lid frame. The cassette also includes a mechanism for releasable maintaining the cassette in the closed position. The porous screen is preferably fabricated from a woven nylon material.

30 Claims, 2 Drawing Sheets 5,427,742

TISSUE PROCESSING CASSETTE

BACKGROUND OF THE INVENTION

1. Field of the Invention

The invention relates to tissue processing cassettes, and, in particular, to tissue processing cassettes adapted for preparing very small tissue specimens for histological examination.

2. Description of the Prior ART

Tissue processing cassettes used for preparing biological tissue specimens for histological examination are well known. Tissue processing cassettes typically include a rectilinear, open-topped box-like base having a perforated bottom wall and a removable perforated cover, or lid. The cassettes are generally fabricated of a moldable plastic that resists damage or reaction from processing solvents and acids or reaction with the tissue specimen. A tissue specimen is typically placed within an enclosure formed by the base and lid and then processed in various solutions appropriate to the tissue and the examination.

The tissue processing steps are generally done in batches with other tissue specimens in a tissue cassette processing container, wherein each tissue specimen is enclosed within its own tissue processing cassette. The processing fluids pass through the perforated bottom walls and lids of the tissue processing cassettes in the processing container. Such treatments can include, for example, fixing, dehydrating, clearing, and infiltrating the tissue specimen with molten paraffin. After the aforesaid processes are completed, the lid is typically removed and the specimen removed to a mold. The mold is also adapted to receive the base, which is typically rectangular-shaped, in a recess in the top of the mold above the specimen. The mold is then filled through the perforations in the base with liquid paraffin or another tissue encasing material. After the paraffin sets, the base, having a block of solidified paraffin encasing the tissue specimen attached thereto, is mounted in a microtome. A pan of the paraffin block, including the specimen, projects beyond the base whereby a section of the tissue specimen can be sliced off for histological examination.

The perforated bottoms and lids of the tissue processing cassettes are typically rigid webs having openings at least about 1.0mm in size in order to allow the processing fluids to flow therethrough. A serious problem arises where the tissue specimen is about the size or smaller than the size of the pores in the base or the lid. The specimen could be lost or washed into a neighboring cassette. Even if the tissue specimen is larger than the pore size, parts of a specimen smaller than the pore size can break away from a larger tissue specimen and migrate to another capsule, thereby contaminating that specimen.

Special procedures are typically employed to resist cross-contamination or loss of very small specimens when preparing such specimens for histological examination. Special procedures can include wrapping the specimen in filter paper or in a sponge, or placing it in a small bag of woven material having a fine mesh. The processes of wrapping and unwrapping or bagging and unbagging of the tissue specimen can distort the specimen, contaminate the specimen, or increase the chance of tissue loss.

U.S. Pat. No. 4,557,903, to McCormick, discloses a tissue processing cassette which includes a pair of interlocking frames, each of the frames having a porous web having a porosity between about 25% and about 75%, preferably fabricated from a non-woven nylon. The web extends across a large rectangular central opening in each of the bottom frame and top frame. The non-woven nylon webbing resists passage of small tissue specimens from one cassette to another neighboring cassette. The non-woven nylon screen must be cut to permit passage of the liquid paraffin during the step of encasing the specimen in paraffin. In addition, when preparing very small tissue specimens for histological examination, the specimen may be lost in a corner of the opening in a frame, making it difficult to locate.

Therefore, there is a need for an alternative to prior art tissue processing cassettes that will permit small tissue specimens, generally less than 1.0 mm in size, to be prepared for a histological examination without cross-contaminating nearby specimens or distorting or losing the specimen from the tissue processing cassette during the processing.

SUMMARY OF THE INVENTION

It is an object of the invention to provide a processing cassette for small tissue specimens.

It is another object of the invention to provide a tissue processing cassette that resists cross-contamination of a tissue specimen contained in the cassette during processing of the specimen with other tissue specimens contained in separate cassettes.

It is another object of the invention to provide a tissue processing cassette that reduces the chances of distorting or losing a tissue specimen during preparation for histological examination.

It is another object of the invention to provide a processing cassette for small tissue specimens that enables the specimen to be visually located within the cassette.

It is another object of the invention to provide a tissue processing cassette that can prepare small samples for histological examination with the same methods used for processing larger tissue specimens.

It is another object of the invention to provide a processing cassette for small tissue specimens that does not require the tissue specimen to be wrapped or bagged prior to processing, or unwrapped or removed from a bag before slicing for histological examination.

These and other needs are met according to the invention for a tissue processing cassette that includes a base frame and a lid frame, each including a central opening and a face adapted to abut the face of the other in registered relationship in a closed position. A porous screen spans the central opening of each of the base frame and the lid frame, the screens being spaced apart when the base frame and the lid frame are in abutment, whereby the base frame, the lid frame and the screens define an enclosed area for holding a tissue specimen during preparation for histological examination. The porous screen permits processing fluids to flow through the enclosure, but resists entry of particulate contaminants into the enclosure, and also resists outflow of a small tissue specimen or a part broken off therefrom, smaller than about 1.0ram, from the enclosure during processing. The enclosure preferably includes an interior wall surface having no sharp corners that may trap a small specimen. The cassette also includes a mechanism for releasable maintaining the base frame and the lid frame in the closed position.

According to another aspect of the invention, an outer frame, preferably about rectangular in shape to fit standard tissue molds and microtomes, and having a substantially larger area than the central opening, includes a web, preferably rigid and porous, for supporting at least one of the base frame and the lid frame.

According to another aspect of the invention, a cassette for holding a tissue specimen during preparation for histological examination includes a pair of outer frames, at least one outer frame preferably being substantially rectangular-shaped in order to fit in an industry standard tissue mold or microtome, wherein each of the outer frames includes an inner frame supported by an inwardly extending rigid web, and each inner frame has a central opening. The outer frames include a mechanism for releasable holding the inner frames closed whereby a face of each of the inner frames abuts the face of the other in registered relationship. A porous screen extends across the central opening of each of the inner frames, the screens being spaced apart to define an enclosure in the closed position. The screens permit flow of processing fluids through the enclosure, while resisting entry of particulate contaminants into the enclosure and loss of the tissue specimen or a fragment thereof from the enclosure. The perimeter wall between the screens of the enclosure preferably includes no sharp corners that can trap a small specimen.

The porous screen can be fabricated from a material having a fine mesh, such as a woven fabric, for example nylon, or a metal screen. The screens preferably permit visual inspection of the position of the specimen within the enclosure.

These and other objects of the present invention will be more fully understood from the following detailed description of the invention with reference to exemplary embodiments as illustrated in the drawings appended hereto.

DETAILED DESCRIPTION OF THE INVENTION

Figure 1:
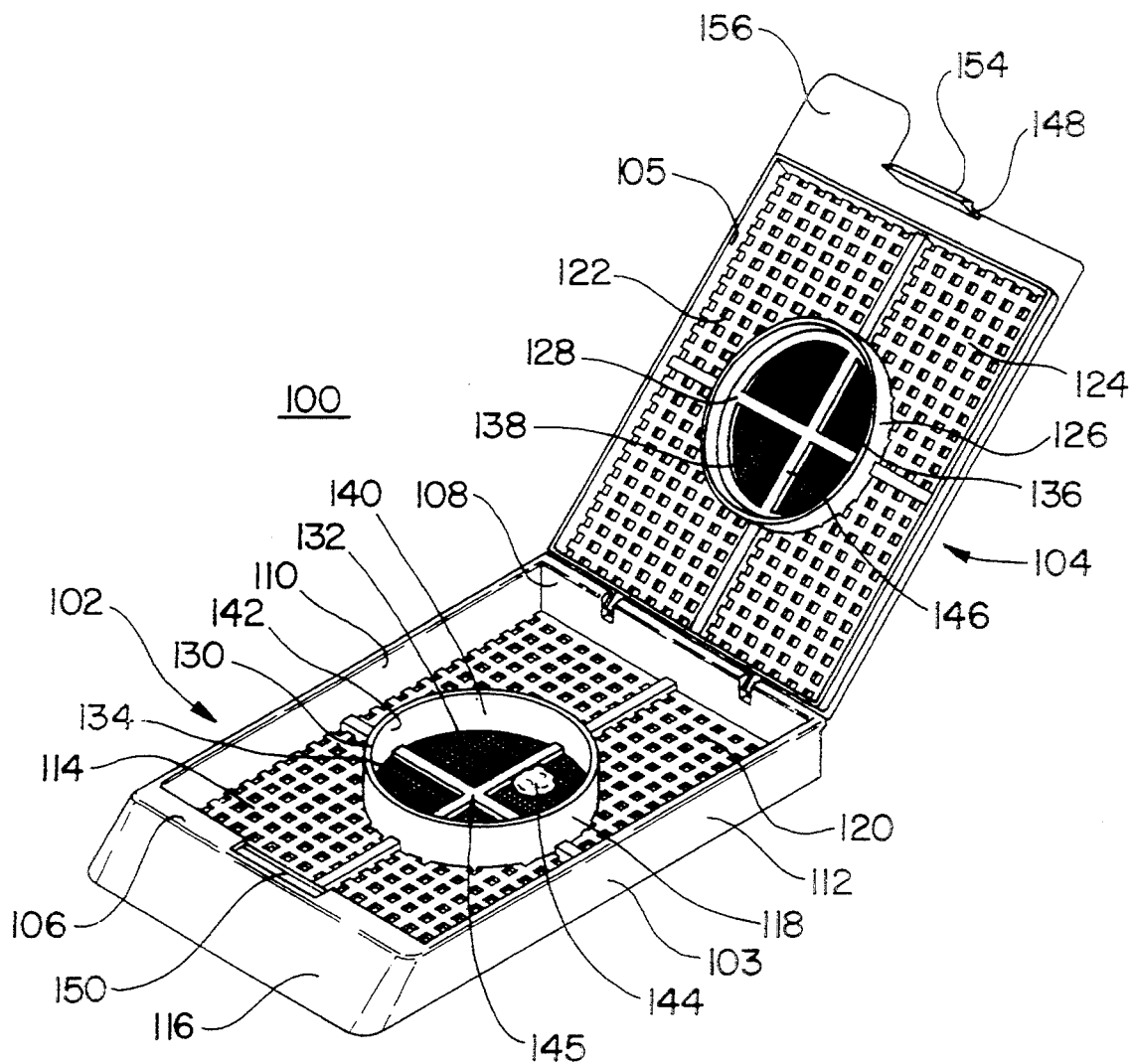
FIG. 1 is a perspective view of a first embodiment of the invention.

Referring now to the drawings, and in particular to FIG. 1, a preferred embodiment of a tissue processing cassette 100 includes a base 102 and a removable lid 104. The base 102 includes a substantially rectangular-shaped outer base frame 103 adapted for placement in an industry standard tissue mold or micritome. The outer base frame 103 has a front wall 106 and a back wall 108, a left side wall 110 and a right side wall 112, surrounding a central base opening 114. The outer surface 116 of the front wall 106 is preferably flat and angled forward to provide a surface for marking indicia identifying a tissue specimen. The base 102 also includes an inner base frame 118 surrounded by the walls 106, 108, 110, 112, that is preferably supported by a rigid base web 120. The inner base frame 118 can also be directly supported by one or more of the walls 106, 108, 110, 112. The inner base frame is preferably centered within the central base opening 114, however it need not be so centered.

The lid 104 includes a substantially rectangular-shaped outer lid frame 105 that defines a central lid opening 122. A rigid lid web 124 supports an inner lid frame 126 within the central lid opening 122. The inner lid frame 126 can also be supported directly from the outer lid frame 105. The inner lid frame 126 has a bottom surface 128 that registers with a top surface 130 of the inner base frame 118 in abutting relationship in a closed position. The inner lid frame 126 substantially surrounds the inner base frame 118 in the closed position.

A first porous screen 132 extends across a central opening 134 of the inner base frame 118 and a second porous screen 136 extends across a central opening 138 of the inner lid frame 126. When the lid 104 is closed over the base 102 such that the bottom surface 128 is an abutment against the top surface 130, the screens are spaced apart to define an enclosure 140 peripherally surrounded by a smooth surface that preferably includes an inner surface 142 of the inner base frame 118. The porous screens 132, 136 have openings small enough to resist outflow of the smallest specimens and also specimen fragments, or floaters, that can break away from a larger specimen during processing. The small opening size of the screens also resist entry into the enclosure of particulate contaminants, such as floaters from other tissue specimens being processed in the same tissue cassette processing container.

The screens are preferably made of a variety of materials, such a fine-mesh metal screen, or a fabric made of natural or synthetic fibers. In a preferred embodiment, the screens are fabricated from an about 30 denier weight woven nylon fabric, having a mesh that is at least about as large as that defined by an about 141 micrometer warp and an about 133 micrometer weft. The use of such woven nylon screens permits fluid flow therethrough, enabling the tissue specimen 144 to be processed for histological examination. The woven nylon screens also permit visual inspection of the placement of a tissue specimen 144 without removing the lid of the cassette 100. Additional support for the screens 132, 136 can be provided by rigid members, such as the illustrated cross members 145, 146, extending across the central openings 134, 138 respectively.

It is important to note that the enclosure 140 into which the tissue specimen 144 is placed for processing has no sharp corners. The tissue processing cassette 100 illustrated in FIG. 1 has a cylindrically shaped enclosure, the inner surface 142 of the inner base frame 118 defining the peripheral wall and the porous screens 132, 136 defining the end walls of the enclosure 140. Because there are no sharp interior corners, small tissue specimens are less likely to be trapped than with prior an cassettes.

The cassette 100 includes means for releasable latching the removable lid 104 on the outer base frame 103 such that the top surface 130 abuts the bottom surface 128 in registered relationship, thereby forming the enclosure 140. The means for removably latching can be provided by any of a variety of well known mechanisms. In the exemplary embodiment illustrated in FIG. 1, the outer lid frame 105 is removably hinged to the back wall 108 of the outer base frame 103 by a hinge post (not shown) on the outer lid frame 105 that fits into an open sided, cylindrical post receptacle (not shown) on the back wall 108. To retain the lid 104 in a closed position, the outer lid frame 105 can include a transversely extending tab 148 that fits into a mating slot 150 in a top face 152 of the front wall 106 of the outer base frame 103. The tab 148 includes a latching mechanism, such as a protrusion 154 that can releasable engage an interior shoulder (not shown) within the front wall 106 of the outer base frame 103. The lid 104 also preferably includes a finger tab 156 to aid in opening and closing the cassette 100 with a finger.

Figure 2:
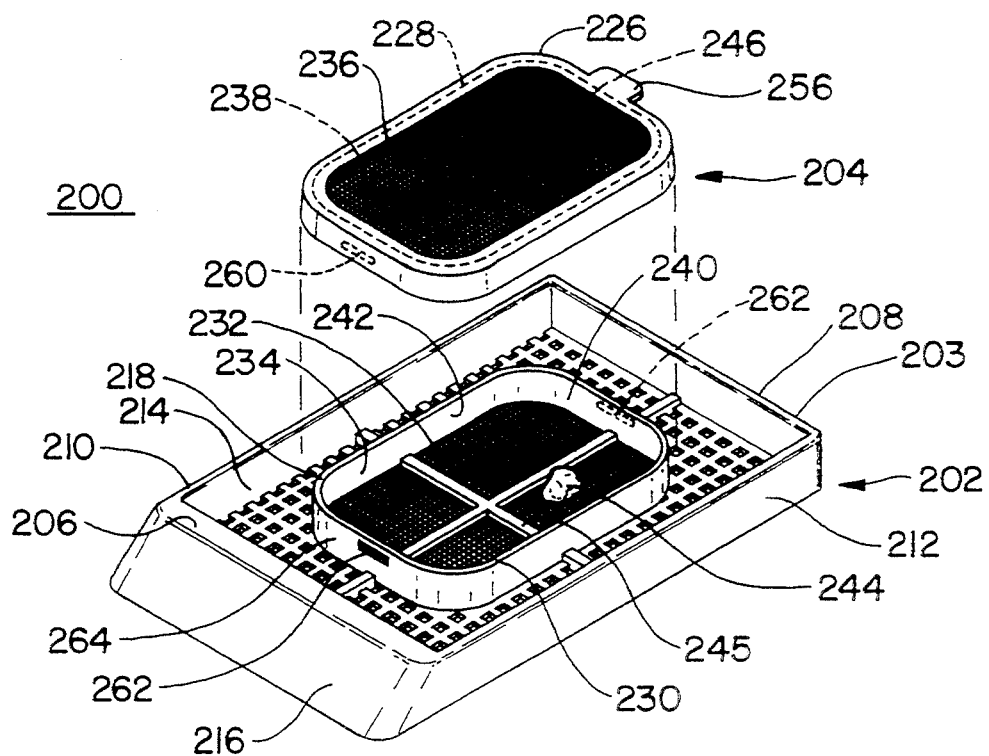
FIG. 2 is an exploded perspective view of a second embodiment of the invention.

A second embodiment of a cassette 200 according to the invention is illustrated in FIG. 2. The base 202 and outer base frame 203 of cassette 200 is similar in most respects to the base 102 and outer base frame 103 of the tissue cassette 100 illustrated in FIG. 1. It includes a front wall 206, a back wall 208, a left side wall 210, and a right side wall 212 that together define a central base opening 214. Within the central base opening 214 is an inner base frame 218 supported by an inwardly extending rigid web 220. The front wall 206 has a sloping from surface 216 that can be used for marking indicia identifying a tissue specimen 244 enclosed in the cassette 200. A removable lid 204 includes a lid frame 226 that directly latches to the inner base frame 218 such that a top surface 230 of the inner base frame 218 abuts a bottom surface 228 of the lid frame 226 in registered relationship when the lid frame 226 is latched to the inner base frame 218. The lid frame 226 substantially surrounds the inner base frame 218 in the closed position. A porous screen 232 extends across a central opening 234 defined by the inner base frame 218 and a similar porous screen 236 extends across a central opening 238 defined by the lid frame 226. Rigid cross members 245,246 provide additional support for the screens. The porous screens 232, 236, the inner base frame 218 and the lid frame 226 define an enclosure 240 for placement of the tissue specimen 244 for processing before histological examination. The enclosure 240 in this embodiment is about rectangular in shape, however, it includes no sharp corners that could trap a small tissue specimen. The inner surface 242 of the inner base frame 218 is preferably smooth.

A latching mechanism that can be used for this embodiment includes inwardly facing tabs 260 on each of the front wall and back wall of the lid frame 226 that engage with indentations 262 in the outer surface 264 of the front and the back of the inner base frame 218. A finger tab 256 is included in the lid 204 to aid in latching and unlatching the lid 204 from the inner base frame 218. Of course, the tabs 260 and indentations 262 can be alternatively located on the sides of the lid frame 226 and the inner base frame 218.

It should be understood that the embodiment illustrated in FIG. 2 can be modified with the inclusion of an outer lid frame and rigid web supporting the inner lid frame 226, similar to the outer lid frame 105 and web 122 illustrated in FIG. 1. The latching mechanism illustrated in FIG. 2 and the placement of the finger tab 256 would also be modified accordingly with the inclusion of these additional features.

Figure 3:
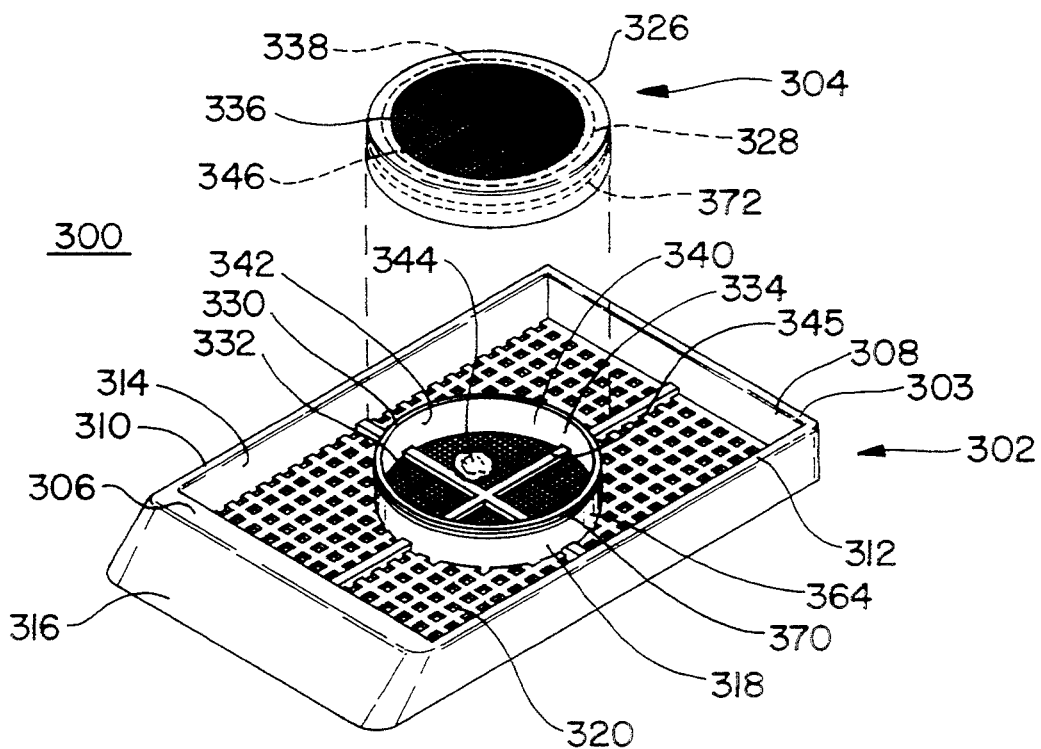
FIG. 3 is an exploded perspective view of a third embodiment of the invention.

A third embodiment of a tissue processing cassette 300 is illustrated in FIG. 3. Cassette 300 is similar to cassette 200 in that it includes a base 302 having a generally rectangular outer base frame 303, the outer base frame including a front wall 306, a back wall 308, a left side wall 310 and a right side wall 312 defining a central opening 314. A front surface 316 of the front wall 306 of the outer base frame 303 slopes forward and can be used for marking indicia for identifying a tissue specimen 344 contained in the cassette 300. An inner base frame 318 is located in the central opening 314 and is supported by an inwardly extending rigid web 320. The inner base frame 318 in this embodiment is circular in shape and has a smooth inner surface 342 free from sharp corners that could possibly trap a small tissue specimen. A circular, removable lid 304, including a lid frame 326 that latches directly to the inner base frame 318 such that a top surface 330 of the inner base frame 318 abuts a surface 328 of the lid frame 326 in registered relationship in the latched position. The latching mechanism illustrated includes threads 370 on the outer surface 364 of the inner base frame 318 mating with threads 372 on the inner surface of the lid frame 326. A porous screen 336 extends across a central opening 338 in the lid frame 326 and a similar screen extends across a central opening 334 in the inner base frame 318. Rigid cross members 345,346 provide additional support for the screens. When the lid 304 is latched to the inner base frame 318 an enclosure 340 for holding a small tissue specimen 344 is defined by the inner base frame 318, the lid frame 326 and the screens 332, 336.

In the embodiments illustrated, the webs 120, 124, 220, 320 are also porous for permitting passage of processing fluids therethrough. The pore size of the webs is not a critical factor of this invention. However, it is important to note that the webs must be rigid for supporting the inner base frame 118, 218, 318 and, in the case of the embodiment illustrated in FIG. 1, for supporting the inner lid frame 126. The rigid parts of the cassettes 100, 200, 300 (not including the screens 132, 136, 232, 236, 332, 336) can be most easily fabricated by molding a relatively rigid polymeric material, such as Delrin acetal, by methods well known in the art. The porous screen is attached to each of the inner base frame and the lid by well known methods, such as, for example, welding, molding, or gluing.

Each cassette base is shaped and sized to fit into a tissue mold or microtome (not shown), such as those generally used in the industry. The outer base frame 103, 203, 303 is preferably 4 cm long and 2.8 cm wide. The sloping front surface 116, 216, 316 of the front wall 106, 206, 306 extends preferably about 7 mm forward at a 45° angle. Each of the back wall 108, 208, 308, the left side wall 110, 210, 310 and the right side wall 112, 212, 312 are preferably about 6mm thick. Cross members in the web of the base and the lid of the embodiment of FIG. 1, are preferably 1 mm in width. The lid frame 104 in the embodiment of FIG. 1 is preferably 3.3 cm long and 2.8 cm wide. The enclosure for holding the tissue specimen in each embodiment is preferably between about 1 cm and about 2 cm across.

A tissue specimen can be processed for histological examination with a tissue processing cassette of this invention according to industry standard methods. A tissue specimen is first placed into an open receptacle formed by the inner base frame 118, 218, or 318 and the porous screen 132, 232 or 332, respectively. The tissue specimen is enclosed in the enclosure 140, 240 or 340, respectively, by covering the inner base frame with the inner lid frame 126, 226 or 326, respectively. The cassette 100, 200 or 300 is placed in the processing container (not shown) for processing with or without other other tissue specimens situated in separate cassettes. The tissue specimen or specimens can then be subjected to processing fluids while situated in their respective enclosures, as described hereinbefore in the section entitled Description of the Prior Art. The final steps before histological examination are removing of the cassette from the processing container, removing the lid, removing the specimen into a mold adapted to receive the base 102, 202 or 302 in the upper section of the mold, encasing the tissue specimen in paraffin by pouring liquid paraffin into the mold through openings in the base 102, 202 or 302, removing the paraffin encased tissue specimen and base from the mold, mounting the base with the paraffin encased specimen in a microtome, and slicing a section of the tissue specimen with the microtome.

Whereas particular embodiments of the present invention have been described above as examples, it will be appreciated that variations of the details may be made without departing from the invention. Therefore, reference should be made to the appended claims rather than to the foregoing discussion of preferred examples, in order to assess the scope of the invention in which exclusive rights are claimed.

I claim:

1. A tissue processing cassette, comprising:
   a base frame and a removable lid frame, each including a central opening and a face adapted to abut the face of the other in registered relationship in a closed position, wherein the base frame includes an inner base frame defining the central opening of the base frame, an outer base frame spaced from and surrounding the inner base frame, and a rigid, porous web supporting the inner base frame from the outer base frame;
   means for releasably maintaining the base frame and the lid frame in the closed position; and
   a porous screen spanning the central opening of each of the base frame and the lid frame, the screens being spaced apart in the closed position with the base frame, the lid frame and the porous screens defining an enclosure for holding a tissue specimen during preparation for histological examination while permitting process fluids to flow through the enclosure, the enclosure being further defined by an interior perimeter wall including no sharp corners between the screens.

2. The tissue processing cassette of claim 1, wherein the porous screen does not span the rigid, porous web.

3. The cassette of claim 2, wherein the base frame includes an outer perimeter that is about rectangular-shaped and sized for placement in a tissue mold, and wherein the screens are fabricated of a woven material for resisting entry of particulate contaminants into the enclosure, resisting loss of tissue fragments from the enclosure.

4. The cassette of claim 3, wherein the central opening of each of the base frame and the lid frame have a cross section that is about circular-shaped.

5. The cassette of claim 3, wherein the central opening of each of the base frame and the lid frame have a cross section that is about rectangular-shaped with rounded interior corners.

6. The cassette of claim 3, wherein the woven material comprises a woven nylon fabric.

7. The cassette of claim 6, wherein the woven nylon fabric is about 30 denier weight and has a mesh that is at least about as large as that defined by an about 141 41 micrometer warp and an about 133 micrometer weft.

8. The tissue cassette of claim 3, wherein the woven material permits visual inspection of the tissue specimen within the enclosure.

9. The tissue processing cassette of claim 3, wherein the woven material comprises a woven, synthetic fabric.

10. A cassette for holding a tissue specimen during processing prior to histological examination, comprising:
    a pair of separable frames, each of the separable frames including an outer frame surrounding an interior frame which defines a central opening and which includes a face abutting the face of the other in registered relationship in a closed position, the interior frame being supported by a rigid, porous web extending inwardly from the outer frame;
    releasable means for holding the separable frames in the closed position; and
    screen means extending across the central opening of each of the interior frames, the screen means being spaced apart and defining, with a round-cornered interior surface of at least one of the separable frames, in the closed position, an enclosure, the screen means resisting outflow of the tissue specimen or a part thereof from the enclosure, resisting entry of particulate contaminants into the enclosure, permitting flow of processing fluids through the enclosure while permitting fluid flow therethrough.

11. The cassette of claim 10, characterized in that the outer frame of at least one of the the separable frames is shaped to fit into a tissue mold.

12. The cassette of claim 10, wherein the screen means does not span the rigid, porous web.

13. The cassette of claim 12, wherein the screen means are fabricated of a woven material.

14. The cassette of claim 13, wherein the woven material comprises a woven nylon fabric.

15. The tissue cassette of claim 13, wherein the woven material permits visual inspection or the tissue specimen within the enclosure.

16. The cassette of claim 13, wherein the woven material comprises a woven, synthetic fabric.

17. The cassette of claim 13; wherein each central opening has a cross section that is about rectangular-shaped with rounded interior corners.

18. A tissue processing cassette for containing a tissue specimen during processing with processing fluids preparatory to histological examination, comprising:
    an inner base frame and a removable inner lid frame, each including a central opening and a face adapted to abut the face of the other in registered relationship in a closed position during the processing;
    base screen means spanning the central opening of the inner base frame and lid screen means spanning the central opening of the inner lid frame, the base screen means and the lid screen means being spaced apart when the inner base frame and the inner lid frame are in the closed position such that the inner base frame, the inner lid frame, the base screen means and the lid screen means define an enclosure for containing the tissue specimen during the processing, each of the base screen means and the lid screen means permitting processing fluids to flow through the enclosure, resisting entry of particulate contaminants into the enclosure, resisting outflow of the tissue specimen or a part thereof from the enclosure during the processing.
    an outer base frame surrounding the inner base frame and including support means for rigidly supporting the inner base frame that comprises a rigid, porous web, the outer base frame being sized and shaped for placement in a tissue specimen mold; and closure means for releasably maintaining the inner base frame and the inner lid frame in the closed position during processing.

19. The tissue-processing cassette of claim 18, wherein the base screen means does not cover the rigid porous web.

20. The tissue processing cassette of claim 18, wherein each central opening has a cross section that is about rectangular-shaped with rounded interior corners.

21. The cassette of claim 18, wherein the outer base frame is substantially rectangular-shaped.

22. The processing cassette of claim 18, wherein the base screen means and the lid screen means each comprise a woven material.

23. The cassette of claim 22, wherein the woven material comprises a woven nylon fabric.

24. The cassette of claim 23, wherein the woven nylon fabric is about 30 denier weight and has an about 141 micrometer warp and an about 133 micrometer weft.

25. The cassette of claim 22, wherein the closure means latches the inner lid frame directly to the inner base frame.

26. The cassette of claim 25, wherein the central opening of each of the inner base frame and the inner lid frame includes an about circular-shaped cross section.

27. The cassette of claim 25, wherein the central opening of each of the inner base frame and the inner lid frame includes an about rectangular-shaped cross section.

28. The cassette of claim 25, wherein the central opening of each of the inner base frame and the inner lid frame includes a round-cornered interior surface for resisting trapping of the tissue specimen during the processing.

29. The tissue processing cassette of claim 22, wherein the woven material permits visual inspection of the tissue specimen within the enclosure.

30. The tissue processing cassette of claim 22, wherein the woven material comprises a synthetic woven fabric.

* * * * *